United States Patent [19]

Guberek et al.

[11] Patent Number: 5,230,343
[45] Date of Patent: Jul. 27, 1993

[54] COLORED MICROSPHERES FOR MEASURING AND TRACING FLUID MIXING AND FLOW

[75] Inventors: Michael P. Guberek, Encinitas; W. Scott Kemper, San Diego, both of Calif.; Gerd Heusch, Essen, Fed. Rep. of Germany

[73] Assignee: Triton Technology, Inc., San Diego, Calif.

[21] Appl. No.: 656,230

[22] Filed: Feb. 14, 1991

[30] Foreign Application Priority Data

Jun. 14, 1990 [DE] Fed. Rep. of Germany ....... 4019025

[51] Int. Cl.$^5$ ..................... A61B 5/026; A61B 5/0275
[52] U.S. Cl. .................... 128/691; 128/666; 250/341; 424/9; 424/423; 436/56
[58] Field of Search ................. 128/691, 692, 666; 436/56; 424/423, 486, 497, 9; 250/461.2, 341; 356/39–40, 317, 318

[56] References Cited

U.S. PATENT DOCUMENTS

| | | | |
|---|---|---|---|
| 3,677,648 | 7/1972 | Dorsch | 356/40 |
| 4,616,658 | 10/1986 | Shell et al. | 128/691 |
| 4,709,703 | 12/1987 | Lazarow, et al. | 128/654 |
| 4,811,741 | 3/1989 | Shell et al. | 128/691 |

FOREIGN PATENT DOCUMENTS

| | | |
|---|---|---|
| 0059032 | 3/1981 | European Pat. Off. . |
| 0194517 | 2/1986 | European Pat. Off. . |

OTHER PUBLICATIONS

Schosser, et al. A Program for the Determination of Cardiac Output Arterio, Computer Programs in Biomedicine 9 (1979) 19–38.

Rudolph and Heymann, The Circulation of the Fetus in Utero, Circulation Research XXI, Aug. 1967

Hale, et al., Evaluation of Nonradioactive, Colored Microspheres for Measurement of Regional Myocardial Blood Flow in Dogs, Circulation, vol. 78, No. 2, Aug. 1988.

E-Z-TRAC, A Non-Radioactive System for Blood Flow Measurement, Product Description of SRP, 435 N. Roxbury Dr. 300, Beverly Hills, Calif. 90210; Presented American Heart Association Nov. 1986.

*Primary Examiner*—Lee S. Cohen
*Assistant Examiner*—Krista Pfaffle
*Attorney, Agent, or Firm*—William C. Fuess

[57] ABSTRACT

Microspheres labeled with a dye for which the absorption spectra is known permit the measurement of blood flows, particularly regional myocardial blood flow (RMBF), without radiation safety concerns and radioactive waste disposal problems. Polystyrene spheres, nominally of diameter 15±0.1 [SD] um and density 1.09 g/ml, are dyed with a fixed quantity, nominally 30 picograms per microsphere, with one of several, nominally 5, colored dyes. The colored microspheres (CM) are injected into the left atrium or into a coronary perfusion. The CM are extracted from myocardium and blood by digestion with KOH and subsequent microfiltration. The dyes are then recovered from the CM within a defined volume of a solvent, and their concentrations are determined by spectrophotometry. The composite absorbance or emission spectra of several dyes are mathematically resolved using matrix inversion. Leaching of dye from the CM was less than 0.1% over a two months period in vitro, and did not occur during 8 hours in blood and myocardium of 4 anesthetized dogs in vivo. For further validation of this method, pairs of CM and RM (15.5±0.1 [SD] um) were simultaneously injected under 5 different RMBF conditions (range: 0–10 ml/(min g)) into the left anterior descending coronary artery of 4 anesthetized pigs, with coronary inflow as a flow-reference, or into the left atrium of 4 anesthetized dogs using aortic blood withdrawal as a reference.

10 Claims, 6 Drawing Sheets

| Color added | Average Slope (Absorbance other color/Absorbance added color)·100 | | | | |
|---|---|---|---|---|---|
| | white | yellow | red | violet | blue |
| white | | -.41 | -.05 | -.05 | -.18 |
| yellow | -2.7 | | -.99 | -.22 | -.76 |
| red | -2.3 | -.93 | | -.18 | -.42 |
| violet | -1.2 | -.93 | -.59 | | -.16 |
| blue | -.16 | -.72 | -.71 | -.59 | |
| Values represent 100 times the slope of the regression equation | | | | | |

FIG. 5

| Color added | Slope | Variation coefficient [%] |
|---|---|---|
| white | 0.957 | 3.636 |
| yellow | 1.028 | 3.346 |
| red | 1.021 | 1.525 |
| violet | 1.009 | 1.287 |
| blue | 0.984 | 1.513 |
| All correlation coefficients were greater than 0.998 | | |

FIG. 6

|  | Recovered dye (%) | | |
| --- | --- | --- | --- |
| Color | Saline | Blood | Myocardium |
| white | 100 | 100.6 ± 0.5 | 99.6 ± 0.8 |
| yellow | 100 | 99.2 ± 1.1 | 99.2 ± 0.8 |
| red | 100 | 100.5 ± 0.7 | 99.5 ± 1.4 |
| violet | 100 | 98.8 ± 1.3 | 100.5 ± 1.8 |
| blue | 100 | 99.3 ± 1.3 | 98.5 ± 2.7 |

Dye recovered after saline perfusion was set 100%
Values are mean ± SD from 4 dog experiments

FIG. 7

| Animal | Slope | Intercept | r-value | SEE |
| --- | --- | --- | --- | --- |
| pig 1 | 0.99 | 0.00 | 0.99 | 0.08 |
| pig 2 | 0.98 | 0.01 | 0.98 | 0.11 |
| pig 3 | 0.96 | 0.05 | 0.98 | 0.17 |
| pig 4 | 1.07 | -0.02 | 0.98 | 0.15 |
| dog 1 | 0.81 | -0.01 | 0.97 | 0.24 |
| dog 2 | 0.86 | -0.17 | 0.99 | 0.31 |
| dog 3 | 0.90 | -0.24 | 0.96 | 0.46 |
| dog 4 | 1.03 | -0.22 | 0.98 | 0.43 |

SEE: standard error of the estimate

FIG. 8

COLORED MICROSPHERES FOR MEASURING AND TRACING FLUID MIXING AND FLOW

REFERENCE TO RELATED APPLICATIONS

The present application is related to U.S. patent application Ser. No. 07/712,004 for a PROCESS FOR MEASUREMENT OF BLOOD CIRCULATION BY NON-RADIOACTIVE MICROSPHERES, which related application is to inventors including the same Gerd Heusch who is an inventor of the invention contained within the present application.

FIELD OF THE INVENTION

The present invention generally pertains to the measurement and tracing of fluid mixing and flow. The present invention particularly pertains to the measurement of regional myocardial blood flow (RMBF), and other blood flows, by the use of nonradioactive, colored, microspheres in a process of blood flow analysis.

BACKGROUND OF THE INVENTION

Most measurements of fluid mixing and fluid(s) flow(s) are direct. One or more fluid flows may simply be measured while such flows are occurring. Alternatively, any mixture that results from the flows of two or more fluids may be analyzed as to its constituent components in order to quantitatively determine the fluid flows that have transpired.

However, direct measurement of fluid(s) flow(s), such as within the blood stream of a living animal, is often impossible. Meanwhile, direct quantitative analysis of the constituent components of complex, or extensive, mixtures of fluids is often prohibitively difficult or expensive. The expense is magnified if many samples must be taken, and analyzed, over time.

Accordingly, modeling or simulation is sometimes used in order to trace the flow, and mixing, of one or more fluids. For example, a dye may be put in ground water and its dispersion may subsequently be observed. From the observed dispersion of the dye a similar dispersion or pollutants, or other less readily detectable fluids, may be imputed.

Another, sophisticated, form of fluid flow and fluid mixing analysis is indirect. A physical marker is put into, or a chemical marker is bonded to, an actual fluid, or fluid component, for which flow and/or mixing is desired to be assessed. The fluid serves as a carrier. When the distribution of the marker is analyzed then the corresponding distribution of the carrier fluid is imputed.

The highest, and most exacting, expression of this indirect method is in medicine, and particularly in blood flow analysis. The blood, and the organs and tissues receiving blood, within a living animal present a system that is very complex in its fluid flow patterns and dynamics, and that is difficult of direct access and measurement. Accordingly, microscopic markers are placed in the animal's blood where they are subsequently distributed to the animal's tissues. The tissues are subsequently harvested, and the prevalence—i.e., the numbers—of the markers are analyzed, producing thereby an indirect indication of the blood flow to the tissue.

Previous systems that have been developed for medical blood flow analysis—discussed in greater detail hereafter—have proven to be both complex and expensive. Because of their cost and complexity, such systems have not been found suitable for use in routine industrial or environmental fluid flow and mixing measurement problems.

However, it should be recognized that the flow of blood, or blood components, within the arteries and veins of a living animal is only different in complexity, and not in the essential nature of fluid flow dynamics, from the flows of fluids occurring within factories, ecosystems, and the like. Accordingly, if a reliable, effective, and inexpensive indirect fluid flow measurement system suitable for use on the difficult problem of blood flow analysis could be developed, then such a system might well have general applicability to the tracing and measurement of fluid flows, and the mixing of fluids, in diverse environments.

2.1 The Measurement of Blood Flow

The reasons for the measurement of blood flow are set forth in U.S. Pat. No. 4,616,658, discussed in greater detail in following section 2.2. The following discussion is adopted from the discussion within that patent.

The measurement of blood flow in experimental animals is often necessary in the fields of pharmacology, physiology, therapeutics and diagnostics. For example, toxicology studies require blood flow measurement to determine the toxicity of various suspected toxic agents. Further, many diagnostic and therapeutic advances have some impact on the flow of blood. It is therefore desirable to take blood flow measurements.

Blood flow measurements can be performed in many anatomical areas, including the brain, heart, lung, gut, kidney, reproductive organs, skin and muscle. One sensitive and specific previous technique involves the use of radioactively labeled microspheres. In one variant of the technique plastic microspheres are marked with a radioactive label and injected into the left atrium of the heart of an experimental animal. The spheres disperse in proportion to blood flow and lodge in the tissue in direct proportion to the blood flow to that tissue. The animal is then sacrificed and the organ(s) of interest is (are) harvested. Blood flow to a particular organ is determined by measuring the level of radioactivity in the organ, which radioactivity is a function of the number of spheres trapped in the organ's capillaries.

Although the use of radioactively labeled microspheres is sensitive and specific, there are several problems and disadvantages associated with the method. First, startup costs are very high, as they include purchase of a gamma counter to measure radioactivity, lead shielding to protect laboratory workers from radiation exposure, complex storage facilities and a high minimum "per order" cost of equipments from manufacturers. These high costs severely limit the availability of this type of blood measurement, generally restricting its use to large laboratories and medical centers.

Second, up to ten successive measurements per animal can be made using radioactively labeled microspheres, due to the overlap between the emission energies of available radiolabels. Moreover, the measurement of even five blood flow stages requires the use of a complex computer program to analyze and separate the data obtained, further limiting the availability of the technique.

Third, radiolabeled microspheres have a limited shelf life, ranging from one week to several months. Even where the shelf life is at the high end of this range, the continuous decay makes continual recalibration of the testing apparatus necessary.

Fourth, laboratory workers using radioactive microspheres are exposed to substantial radiation danger because many of the isotopes used as labels emit high levels of energy. Accordingly, the costs, and risks, involved in minimizing radiation exposure are substantial.

Finally, and perhaps most critically, disposal of the experimental animals poses significant problems, ecologically, logistically and financially. Because the entire animal carcass remains radioactive for several years after disposal, it must be placed in a special low level radiation dump, to which dumps there is increasing public antipathy. The cost of disposal is becoming prohibitively high, recently ranging to as high as $550 U.S. per animal.

2.3 Particular Previous Methods of Blood Flow Measurement

In 1967, plastic, radioactively labelled microspheres (RM) were introduced for the measurement of regional perfusion. See Rudolph A. M., Heymann M. A.: The circulation of the fetus in utero: Methods for studying distribution of blood flow, cardiac output and organ blood flow. Circ Res 1967;21:163–184.

One year later, Makowski et al introduced a blood withdrawal technique for the quantification of regional blood flow. See Makowski E. L., Meschia G., Droegemueller W., Battaglia F. C.: Measurement of umbilical arterial blood flow to the sheep placenta and fetus in utero: Distribution to cotyledons and the intercotyledonary chorion. Circ Res 1968;23:623–631.

In 1969, Domenech et al first validated the use of radioactive microspheres (RM) for the measurement of regional myocardial blood flow (RMBF). See Domenech R. F., Hoffman J. I. E., Noble M. I. M., Saunders K. B., Henson J. R., Subijantos: Total and regional coronary blood flow measured by radioactive microspheres in conscious and anesthetized dogs. Circ Res 1969;25:581–596. Thereafter, this method has become the standard technique for the measurement of RMBF in various experimental settings. However, due to the precautionary measures needed to minimize radiation exposure, use of RM is restricted to specially licensed laboratories. Storage of the radioactive microspheres, as well as disposal of radioactive waste, is expensive and an environmental hazard.

To avoid some of these limitations inherent to the RM method, U.S. Pat. No. 4,616,658 to Shell et al for NON-RADIOACTIVELY LABELED MICROSPHERES AND USE OF SAME TO MEASURE BLOOD FLOW describes a method for measuring RMBF using non-radioactive, colored microspheres (CM). Later, Hale et al describe a similar technique. See Hale S. L., Alker K. J., Kloner R. A.: Evaluation of nonradioactive, colored microspheres for measurement of regional myocardial blood flow in dogs. Circulation 1988;78:428–434.

According to the techniques of Shell et al and Hale et al, microspheres may be labeled with colored dyes, and subsequently visually identified and counted in tissue, either after separation therefrom or while still trapped in the tissue's capillaries. Shell et al also describe labeling microspheres by linkage to enzymes, particularly plant enzymes, and, after extraction from tissue, measuring the density of enzyme-linked spheres by a measurement of optical density which is indicative of enzyme activity.

In the previous techniques using non-radioactively labeled colored microspheres (CM), tissue samples that have captured microspheres from the circulating blood of a live animal are surgically harvested and are then digested by a combination of enzymatic and chemical methods. Aliquots of the microspheres trapped within a given sample are then counted in a hemacytometer by an investigator using light microscopy, or, in the case of enzyme-linked microspheres, by measurement of optical density to determine enzyme activity.

There are, however, significant limitations to these previous techniques. First, RMBF is extrapolated from only a small aliquot of the colored microspheres (CM) actually trapped within the sample, thereby entailing a substantial statistical error in RMBF calculations. Second, the use of only three different colors has been validated, and then in only a small number of samples, whereas it is clearly desirable to be able to make more than three measurements of RMBF in many experimental protocols. Third, there is a considerable variation in the diameter of the CM used in previous studies, as admitted by Hale et al. Fourth, the prior methods require substantial time for the tedious counting of individual colored microspheres. Fifth, in preliminary experiments, the inventors of the present invention found it almost impossible to distinguish visually the nine (9) commercially available microsphere colors in the reddish background of digested myocardium.

Recently, still another alternative non-radioactive method for measuring RMBF was developed by Morita et al using X-ray fluorescence excitation of microspheres loaded with elements of high atomic number. See Morita Y., Payne B. D., Aldea G. S., McWattes C., Huseini W., Mori H., Hoffman J. I. E., Kaufmann L.: Local blood flow measured by fluorescence excitation of nonradioactive microspheres. Am J Physiol 1990;258:H1573–H1584. So far, only two different labels have been reported to have been validated by comparison to RM after intracoronary injection in two dogs. The method of Morita et al could be hampered by leaching of the label from the microspheres over time. Another disadvantage is the need of a sophisticated and relatively expensive equipment for X-ray excitation and fluorescence detection which is not commercially available.

The previous blood flow analysis methods employing colored microspheres, including the method of Morita et al, require that the numbers of microspheres per unit portion of a recovered tissue sample should be determined. Because the numbers of microspheres introduced within the blood, and captured within the capillaries of the tissue, are enormous, and on the order of $10^6$, the actual numbers are commonly only estimated by statistical sampling, which induces measurement error. Worse, even the determination of the numbers of colored microspheres that are within minute samples is tedious and expensive, involving in the methods of Shell et al and of Hale et al manual observations through a microscope.

In order to circumvent these limitations, it would be desirable if a new method of producing and/or using microspheres, and of measuring RMBF therewith, could support both (i) easy tissue processing and (ii) quantitative, automated, and easy counting of all the microspheres within an individual sample. Such a new method would desirably be both economical and validated by a rigorous comparison to RM over a range of RMBF from 0 to 10 ml/(min g) on many hundreds, or thousands, of individual myocardial samples. If such a method were to be suitably economical, reliable, easy to use, and devoid of significant drawbacks, then it might find general use in the measurement and analysis of diverse fluid flow and fluid mixing problems other than only medical problems.

SUMMARY OF THE INVENTION

The present invention contemplates replacing a measurement of the numbers of non-radioactively labeled microspheres during a use of such microspheres in fluid flow analysis, and particularly in Regional Blood Flow Analysis, with, instead, a measurement of the amount of a colored, non-radioactive, dye that is carried by such microspheres.

In particular, the present invention contemplates (i) dying microspheres with a color for which the quantitative photometric spectrum is known, (ii) introducing the labeled and colored microspheres (CM) so created in a fluid flowing into a volume serving as a reservoir of such fluid, (iii) determining after the introduction of the CM the concentration of dye within the fluid (concentration being the amount of dye per unit time per unit portion of fluid), (iv) recovering at least a sample of the volume, and recovering the CM from a quantized portion of this sample, (v) extracting the colored dye from the recovered CM with a solvent, and (vi) measuring in an automated spectrophotometric procedure the quantitative photometric spectrum of the recovered dye as a quantitative indication of the abundance of the dye within the portion of the sample, and within the sample. The quantitative rate of the flow of that fluid within which the CM were previously resident into the volume can then be calculated.

When the (ii) introducing of the CM is in the circulating blood of a live animal, and when the (iii) determining is of the concentration of dye within the reference withdrawal blood sample, and when the (iv) recovering of the CM is from harvested animal tissue and blood by process of tissue and blood processing, then the (vi) measuring serves as a quantitative indication of the abundance of the dye in the harvested tissue and blood. An ensuing calculation is thus of the rate of the flow of blood within which the CM, and the dye, were contained to the harvested tissue.

The (i) coloring may usefully be of each of several different types of microspheres: the microspheres of each type becoming labeled with an associated one of a plurality of different colors. The quantitative photometric spectrum of each color is both a) individually known, and b) distinguishable from the photometric spectrum of all other colors. When the (ii) introducing, and the (iv) recovering, are of the several different types of microspheres—either of which steps may transpire separated in time and/or space, and may be repeated—then the (vi) measuring in an automated spectrophotometric procedure is of the composite quantitative photometric spectra of the several recovered dyes. Accordingly, the method is expanded to include the additional step of (viii) analyzing the composite spectra, preferably by a computerized mathematical process of matrix inversion, so as to determine the individual spectrums contributory thereto. Such individual spectrums continue to be a quantitative indication of the abundance of the dye associated with each individual type of labeled CM, and a corresponding indication of the flow of that (those) fluid(s) within which each type of CM was previously resident into the volume.

Notably, the (vi) measuring and (viii) analyzing steps are, despite being easy and automated, fully capable of simultaneously determining the absolute, and relative, abundances of a number of different types of dye which are within a corresponding number of different types of CM. These different types of CM may be of different sizes, densities, shapes, or surface characteristics—each of which may have correspondingly different propensities to lodge within tissue or other material (such as soil) within the volume. The different types of CM may have been placed within several different flowing fluids that were subsequently mixed. The different types of CM may have been placed within the same stream of flowing fluid at different times. Accordingly, just one automated photometric analysis readily yields an abundance of temporal and spatial information regarding fluid(s) flow(s) and fluid mixing. Such abundant information is, in particular, eminently suitable for medical blood flow analysis including regional myocardial blood flow (RMBF) analysis, but is not so limited.

The method of the invention has been validated by its production of quantitative results that are in close correlation to RMBF measured by radioactive microspheres after intracoronary injection in 4 pigs ($r=0.98$), and after intraatrial injection in 4 dogs ($r=0.97$). The method of the invention avoids all problems related to radioactivity, is fast and automated, and is cost-effective.

In one of its aspects the present invention is embodied in a process for measuring a rate of a flow of fluid into a volume serving as a reservoir of the fluid. (A fluid flow amount is obviously determinable as the fluid flow rate times elapsed time.) The process includes the steps of (i) labeling microspheres by dyeing the microspheres with a dye having a known photometric spectrum, (ii) introducing the labeled microspheres into the stream of fluid flowing into the volume that serves as the reservoir for the fluid, (iii) first-determining the amount of dye that is within a unit portion of the stream of fluid per unit time at the time of introduction (i.e., the dye concentration), (iv) recovering a sample including fluid from the volume of, which sample had been supplied with fluid prior to its recovery, (v) quantifying a portion of the recovered sample, (vi) extracting the dye from all of such undetermined number of labeled microspheres as are within the quantified portion of the recovered sample, (vii) quantitatively measuring the photometric spectrum of the extracted dye in order to second-determine the amount of dye that contributed thereto, and that was present within the quantified sample portion, and (viii) calculating the fluid flow to the sample as the second-determined amount of dye per quantized sample portion over the first-determined amount of dye per unit time per unit portion of fluid.

As a further elaboration of the method, an interval during which a fluid having the first-determined concentration of dye is permitted to flow into the volume is timed, and the fluid flow into the volume per unit time is calculated in consideration of the timed interval and the second-determined amount of dye accumulated within the volume over a measured time interval.

Notably, the (vii) quantitative measuring of the photometric spectrum may be either of an absorption, or of an emission, spectrum. In the later case the dyed microspheres are fluorescent.

In another of its aspects, the present invention is embodied in a process of labeling microspheres by dyeing a quantity of microspheres with a dye that has a predetermined photometric spectra, therein establishing that the microspheres will thereafter collectively produce a photometric spectrum that is dark or light dependent upon the abundance of the labeled microspheres. The sense of the spectral density is reversed dependent upon whether the dye is absorbing, or emitting (fluorescent, when appropriately radiatively stimulated), of light. The quantities of the microspheres, and the dye, may optionally be predetermined making thereby that a predetermined amount of the dye is taken up by each individual microsphere—but this is not mandated. Normally about 30 picograms dye is absorbed by each typically polystyrene microsphere of diameter 15±0.1 [SD] um and density 1.09 g/ml.

In still another of its aspects, the present invention is embodied in an semi-automated method of measuring (i) the concentration, and, further, (ii) the amount, of microsphere-borne dye within a sample of material, typically animal tissue. The dye has a known photometric spectrum. The steps of a complete method directed to determining both concentration and amount include (i) quantifying a unit portion of the material sample within which sample an undetermined number of the dye-colored microspheres are present, (ii) extracting the microspheres from the unit portion of the material, (iii) drawing off the dye content of the extracted microspheres into a predetermined volume of solution, forming thereby a dye-solution, (iv) measuring in an automated photometric procedure the photometric spectrum of the dye-solution as an indication of the concentration of dye therein, and (v) first-calculating, in consideration of the measured concentration of dye and the predetermined volume of solution, the corresponding total amount of dye that was within the solution, and within the extracted microspheres. If the predetermined amount of dye that was within each microsphere is known, then the method can be still further extended to (vi) second-calculating from the first-calculated total amount of dye, and from the predetermined amount of dye that is within each microsphere, the amount of dye that was within the unit portion of the material, and, imputedly, the amount of fluid carrying CM bearing such dye that was within the unit portion of the material.

The present invention is still further embodied in nonradioactive, colored, microspheres consisting essentially of polystyrene spheres of predetermined size where each microsphere is labeled with a dye having a known photometric spectrum. A plurality of such nonradioactive, quantitatively-dye-labeled, colored microspheres of different types are suitable for use—all at the same time—in a time-overlapping plurality of fluid flow, and more particularly regional myocardial blood flow, measurements. In such a use each individual type of the plural different types of microspheres is made from (i) a plurality of substantially identical polystyrene spheres of a predetermined identical size, labeled with (ii) an associated one of a like plurality of different dyes, each of the plurality of dyes being individually associated with a corresponding one of the plurality of microsphere types.

Because each dye has a known photometric spectrum that is distinct from the photometric spectrum of all others of the plurality of dyes, a composite absorbance spectra of all such dyes together may be suitably analyzed—including specifically by the mathematical technique of matrix inversion—so as to determine the relative abundance of each such dye.

These and other aspects and attributes of the present invention will become increasingly clear upon reference to the following drawings and accompanying specification.

BRIEF DESCRIPTION OF THE DRAWINGS

FIG. 2b is a graph showing the contributions of the five (5) different colors to the composite spectrum previously seen in FIG. 2a.

FIG. 3b is a graphical plot of percentage residuals versus estimated flow for all data points of FIG. 3a.

FIG. 4b is a graphical plot of percentage residuals versus estimated flow for all data points of FIG. 4a.

DESCRIPTION OF THE PREFERRED EMBODIMENT

The present invention involves the quantitative measurement of fluid flow, and particularly blood flow, and even more particularly regional myocardial blood flow, by use of microspheres that are colored with a quantitatively-known amount of dye. The photometric spectrum of absorbance, or of emission, of the dye is known.

1. Preparation of Colored Microspheres (CM)

Polystyrene microspheres (15±0.1 um, mean±SD) (Dynospheres, Dyno Particles A S, Lillestrom, Norway) were purchased as a 10% aqueous suspension from Paesel GmbH & Co, Frankfurt, FRG. 500 ul (approximately $28 \times 10^6$ microspheres) of the colorless microsphere suspension were put into a closed, non-airtight test-tube. For purification, the microspheres were washed twice with 70% ethanol and vacuum dried. The microspheres were then dyed with one of five different colors: white (Blankophor MAR), yellow (Resolin-Brilliant-Gelb 10GN 200%), violet (Resolin-Rot-Violett FBL 200%) and blue (Resolin-Brilliant-Blau BGLN 200%) obtained from Bayer AG, Leverkusen, FRG, and red (Terasil Rot EBST) obtained from CIBA-GEIGY AG, Wehr, FRG. For purification prior to use, the yellow and blue dyes were recrystallized in dicholoromethane. For dyeing of red or violet microspheres, 400 mg of the dye, 2 ml aqua bidestillata and 1 ml of a 1% aqueous emulsion of Levegal PTN (Bayer AG, Leverkusen, FRG) were combined in the test-tube containing the dried microspheres from 500 ul of the original suspension. For white and blue microspheres, 8 ml of a solvent-mixture of toluene/dimethylformamide (DMF) (85/15% by volume), saturated with the dye at 80° C. (white dye) or 100° C. (blue dye), were added to the dried microspheres. For yellow microspheres, 100 mg of the dye and 1 ml 1,2,4-trichlorobenzene were added to the dried microspheres. These mixtures were then heated in a boiling water bath for 5 (yellow dye) or 90 minutes (white, red and violet dye) or in a paraffin bath at 125° C. for 90 min (blue dye). The white, yellow and blue microspheres were recovered by filtration through polyester microfilters (pore-size 8 um, diameter 47 mm, Nuclepore, Tubingen, FRG). Any remaining free dye between the filtered microspheres (white, yellow, blue) or the solution containing the red and violet microspheres was washed out with absolute ethanol. For that purpose, the microspheres were suspended in absolute ethanol, ultrasonicated, centrifuged (3 min, 2500 g) and the supernatant drawn off. The purified CM were vacuum dried, resuspended in the isodense solution (see above), ultrasonicated and divided into appropriate portions, i.e. 4 portions containing approximately $7 \times 10^6$ CM each, for later use in an experiment. Microspheres were washed twice with 70% ethanol and vacuum dried before their final suspension in physiological saline solution for injection. This ratio of dye to microspheres produces a defined amount, approximately 30 picograms, of dye on each microsphere.

Figure 1:
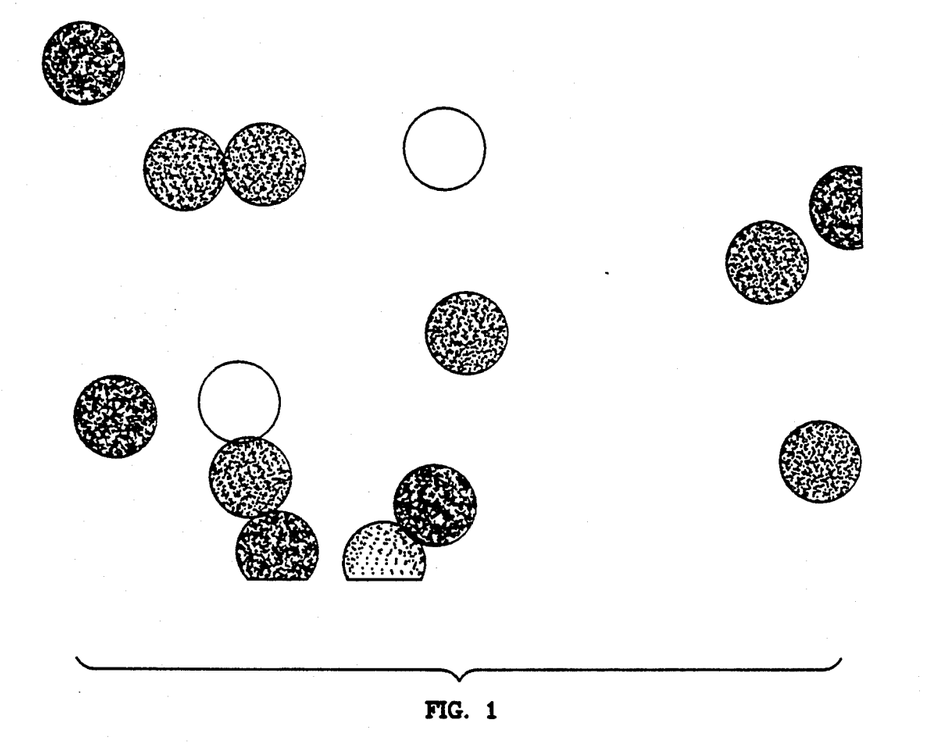
FIG. 1 is a photomicrograph of a mixture of five (5) different colors of colored microspheres (CM) in accordance with the present invention at a magnification of 1,100.

A photomicrograph of a mixture of CM of different colors is shown in FIG. 1. The amount of the above dyeing reagents can be extrapolated up to the production of $100 \times 10^6$ CM. A portion of dried microspheres of each color has been stored for more than 12 months without any effect on their usability.

To test the stability of dye-attachment to the microspheres in vitro, $5 \times 10^6$ CM of each color were suspended in 2 ml saline and stored for two months. When analyzing the dye content in the supernatant after microfiltration of four 2 ml samples for each color, less than 0.1% of dye was recovered. To test the homogeneity of staining, the difference in dye recovered from 6 aliquots containing 400–1000 CM of each color was determined and found to be less than 1.5%.

The density of our CM is 1.09 g/ml, as measured by density gradient centrifugation. To test for potential alterations in the size distribution by the chemical, mechanical and thermic dyeing procedures, 2000 microspheres dyed with different colors were examined by scanning electron microscopy. The small deviation from the average size of 15 um, which was indicated by the manufacturer (15±0.1 [SD] um), was confirmed. There were no microspheres smaller than 14 um and only 8/2000 as large as maximally 17 um. In 100 RM (DuPont NEN Products, Dreieich, FRG) which were used for comparison, the small deviation from the average size indicated by the manufacturer (15.5±0.1 [SD] UM), was also confirmed.

2. Quantification of CM

CM are quantified by their dye-content. Dye is recovered from the microspheres by adding 100 ul DMF as a solvent with a Hamilton syringe (Microlab P, Hamilton, Bonaduz, CH). To ensure complete recovery of the dye, it is preferable to put the CM and DMF together into a conical centrifuge tube and vortex-mix the mixture for 30 s. The tube is then centrifuged (5 min, 2000 g) and the dye-solution transferred into 0.3 ml glass tubes (JWGE 19165 Millipore, Eschborn, FRG). Finally, the transferred dye-solution is separated from remaining particles and microspheres by centrifugation (3 min, 2000 g) in order to minimize scatter in the subsequent spectrophotometry.

The completeness of dye-removal from the microspheres was tested by adding increasing amounts of the DMF solvent from 50 to 800 ul in 8 samples of dried CM, and by exposing the CM to DMF for increasing durations from 20 s to 1 hour. Confirming the completeness of dye-removal from the microspheres by 100 ul DMF for a few minutes (30 s vortex agitation plus 3 min centrifugation), no increase in dye-removal occurred with increasing amounts of DMF and increasing duration of exposure to DMF.

The photometric absorption of each dye-solution was determined by a Diode-array UV/Visible Spectrophotometer (Model 8452A, Hewlett Packard) (wave length range: 190–820 nm, 2 nm optical band width). In a manner similar to the overlap correction in counting the RM, the composite spectra (FIG. 2a) of each dye-solution was resolved into the spectrum of the single constituents (FIG. 2b) by a matrix inversion technique. See Schosser R., Arfors K. E., Messmer K.: MIC-II—A program for the determination of cardiac output, arterio-venous shunt and regional blood flow using the radioactive microsphere method. Comput Programs Biomed 1979;9:19–38.

Figure 2A:
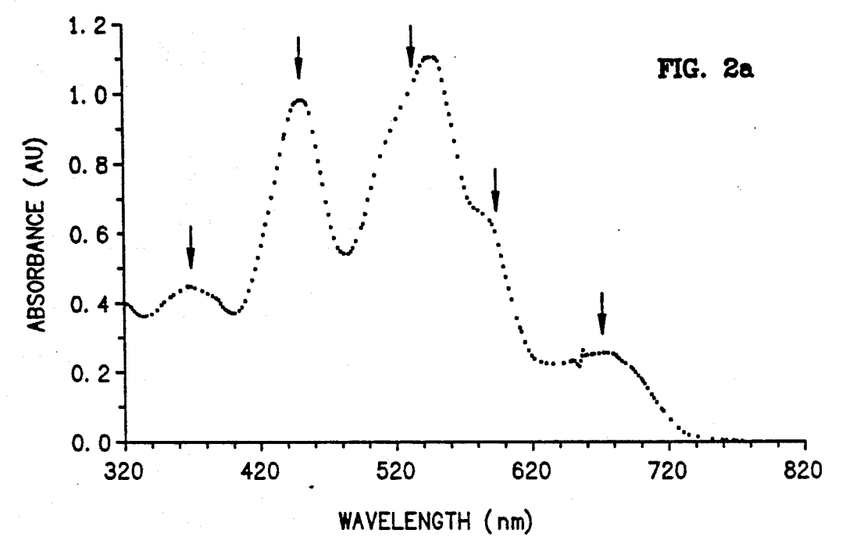
FIG. 2a is a graph of a composite spectrum of five (5) different colors of the dye-solution recovered from the CM of an individual sample.
Figure 2B:
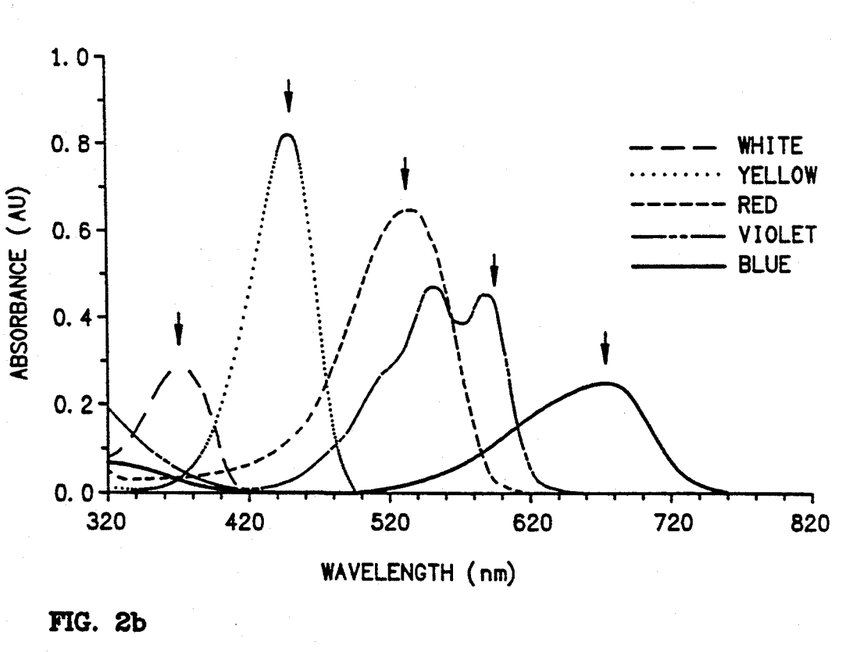

The absorption spectrum of each dye was measured separately and served as a reference for the matrix inversion, determining the contribution of each color to the measured composite spectra at five fixed wavelengths: 370, 448, 530, 594 and 672 nm (arrows in FIG. 2a and FIG. 2b). Within 10 s 100 single measurements of 0.1 s duration, each were performed and averaged, such that the standard deviation of each absorbance value was less than 0.1% of the mean. The amount of dye or the number of CM in a given sample were adjusted to achieve absorbance values of no more than 1.3 AU (absorbance unit, 1 AU=−1 g(10% light transmission/100%)) and thus assure the linearity between absorbance and dye concentration according to the Lambert-Beer law. Samples with absorbencies higher than 1.3 AU were diluted and analyzed again. The lower limit of detection which could be reliably distinguished from background noise was 0.05 AU.

To test the error of separation by spectrophotometry and matrix inversion resolution of composite spectra, an overdetermined set of linear equations as previously applied by Baer et al to RM was used. See Baer R. W., Payne B. D., Verrier E. D., Vlahakes G. J., Molodowitch D., Uhlig P. N., Hoffman J. I. E.: Increased number of myocardial blood flow measurements with radionuclide-labeled microspheres. Am J Physiol 1984;246:H418–H434.

Therefore, the absorbance of each color in the dye-solution was determined at three different wavelengths:

at the normally used wavelength as described above, as well as at the wavelengths 10 nm above and below this wavelength. A prerequisite for this approach is an equal variance of absorbance or a normalization with respect to the variance. Therefore, the square of the difference between the measured and the calculated absorbance values was weighted with the variance of 100 consecutive measurements. It must be realized that the variance of consecutive measurements of the same amount of absorbance using the CM-technique is a different kind of variance than that of increasing durations of counting radioactivity using the RM-technique. Nevertheless, the goodness of fit, or so-called chi-squared, was determined in the same way as described by Baer et al, supra, for RM.

To test potential interactions of different colors within a composite spectrum, six (6) increasing concentrations of a fifth dye were added to a given four colorset. A linear regression analysis was performed between increasing absorbance of the added fifth color and the absorbance of the remaining four colors, using mean values of sixfold determinations for each added color.

To test the completeness of recovery of each dye by the matrix inversion resolution of a composite spectrum, the same set of data was used. The increase in total absorbance after addition of a fifth dye to a given four color-set was measured. After calibration of total absorbance within the spectral range with the absorbance value at the predetermined wavelength for each color separately, the measured increase in total absorbance after addition of a fifth color could be compared to the absorbance value attributed to this fifth color by matrix inversion resolution of the composite spectrum.

3. In vivo-validation of CM in accordance with the invention

Animals used in a study of the effectiveness of CM in accordance with the invention were handled in accordance with the guidelines of the animal welfare regulations of the American Physiological Society, and the experimental protocol was approved by the bioethical committee of the district of Dusseldorf, FRG.

3.1 Protocol 1 —stability of dye-attachment in vivo

Four beagle dogs (13–18kg body weight) were anesthetized using thiamylal sodium (15 mg/kg) administered through a brachial vein. An endotracheal tube was positioned and connected to a respirator equipped with an enflurane vaporizer (Spiromat 650, Drager, Essen, FRG). Anesthesia was maintained using enflurane (0.5–1.5%) with a mixture of nitrous oxide and oxygen, and ventilation was adjusted to keep $pCO_2$ between 35 and 50 mmHg, pO, above 100 mmHg and pH within the normal range. One common carotid artery was cannulated with a large polyethylene catheter which served as the blood supply for an extracorporeal circuit. The other carotid artery was cannulated with a small polyethylene catheter for pressure measurement (Bell & Howell, Type 4-327-I, Pasadena, Calif.) and blood sampling. An internal jugular vein was cannulated to return blood from the extracorporeal circuit prior to coronary cannulation and a second jugular vein was cannulated for saline infusion.

A left lateral thoracotomy was performed in the fourth intercostal space and the pericardium was opened and sutured to cradle the heart. A cathetertip-manometer (Braun-Melsungen, Type 501-869/2) was placed in the left ventricle though the right femoral artery for measurement of left ventricular pressure. The first derivative of left ventricular pressure (dP/dt) was calculated from digitized left ventricular pressure data using CORDAT software (Reference Schulz R., Hucking G., Heusch G.: "CORDAT"—a new data acquisition and reduction program. Eur Heart J 1989;10:309.) on an AT-type personal computer.

Ultrasonic crystals were implanted in the anterior wall within the perfusion area of the left anterior descending coronary artery (LAD) to measure midwall segment shortening using standard techniques. See Sasayama S., Franklin D., Ross J. Jr., Kemper W. S., McKown D.: Dynamic changes in left ventricular wall thickness and their use in analyzing cardiac function in the conscious dog. Am J Cardiol 1976;38:870–879. See also the operating instructions for System 6 available from Triton Technology, San Diego, Calif.

A second set of ultrasonic crystals was implanted in the posterolateral wall within the perfusion area of the left circumflex coronary artery. The proximal LAD was dissected free from surrounding tissue for a distance of approximately 1 cm. After heparinizing the dogs (20,000 IU bolus; 10,000 IU hourly), the LAD was ligated and rapidly cannulated. Perfusion pressure was measured through a distal side arm of the cannula. Blood was supplied by an extracorporeal circuit with two side ports: one for microsphere injection and one for regional drug infusion. The extracorporeal circuit included an occlusive pump (Masterflex, Cole-Parmer Instrument Co., Chicago, Ill.), which was servo-controlled to regulate coronary pressure, and a 50 ml windkessel. The microsphere injection port was just distal to pump and windkessel in the extracorporeal circuit, and a mixing-chamber with a vortex mixer was positioned just distal to the injection port. Thorough mixing of microspheres with blood by this perfusion system has been documented previously. See Schulz R., Miyazaki S., Miller M., Thaulow E., Heusch G., Ross J. Jr., Guth B. D.: Consequences of regional inotropic stimulation of ischemic myocardium on regional myocardial blood flow and function in anesthetized swine. Circ Res 1989;64:1116–1126.

Arterial and left ventricular pressure, coronary arterial pressure, coronary blood flow to the LAD and segment length of the anterior and the posterolateral wall were recorded on an eight channel recorder (Model MK 200 A, Gould, Oxnard, Calif.) and on-line converted to digital data for subsequent analysis using the CORDAT software.

To test for a potential leaching of the dyes from the microspheres in blood or in tissue, comparisons between CM dissolved in saline and immediately processed and CM which were injected into and kept in blood or myocardium were performed. Previously portioned and dried CM were resuspended in 9 ml saline containing 0.02% Tween 80 and ultrasonicated for 1 min. Prior to their injection, CM were thoroughly dispersed by vortex-mixing and 1.5 ml of this suspension were drawn up with an automatic Hamilton syringe. As indicated by the manufacturer, this syringe can reproducibly draw up the same volume of a fluid with an error of less than 0.3%. Identical (within this range of accuracy) amounts of CM were then injected: a) through a saline-filled copy of the perfusion system from the microsphere injection port to the cannula tip, and the perfusion system flushed with 50 ml saline; b) through another copy of the perfusion system filled with freshly withdrawn heparinized blood, and the perfusion system flushed with 50 ml blood; and c) into the above-described coronary perfusion line of 4 anesthetized dogs. The number of injected CM varied between 75,000 (red), 330,000 (white), 400,000 (violet), 500,000 (yellow) and 550,000 (blue) to account for their different absorbance characteristics. The saline and blood perfusates were collected in teflon-sealed 16 ml screw-cap glass tubes (Schott, Mainz, FRG) in 3.5 ml portions. The saline samples were immediately processed and served as the 100% reference. The blood samples were stored for 8 hours. Prior to euthanization by KCl injection, the LAD perfused myocardium was delineated by methylene blue injection into the perfusion line. The entire delineated area was then removed and further processed.

3.2 Protocol 2 —comparison of CM to RM after intracoronary injection

Four swine (25–35 kg body weight) were initially sedated using ketamine hydrochloride (30 mg/kg i.m.) and then anesthetized using thiamylal sodium (250–500 mg) administered through an ear vein. A tracheostomy was performed through a midline cervical incision, an endotracheal tube positioned and connected to a respirator equipped with an enflurane vaporizer. Anesthesia was maintained as described above. The further instrumentation was also identical to that described above for the four beagle dogs, except that transmural wall thickening was measured instead of midwall segment shortening.

3.3 Protocol 3—comparison of CM to RM after left atrial injection

Four beagle dogs (15–18 kg body weight) were anesthetized and instrumented as described above. However, in these four dogs the LAD was not cannulated for perfusion, and coronary arterial inflow was measured with an electromagnetic flow probe (Statham, Gould, Oxnard, Calif.). Microspheres were injected through a teflon catheter into the left atrium. A second teflon catheter was inserted into the descending aorta for withdrawal of reference blood samples.

Regional myocardial blood flow distribution in protocols 2 and 3 was measured using 15.5±0.1 [SD] um RM labelled with one of the following radionuclides: $^{141}Ce$, $^{51}Cr$, $^{95}Ru$, $^{95}Nb$, $^{46}Sc$, simultaneously with one of the CM. For each intracoronary injection in the four pigs, approximately 130,000 RM were injected. The number of CM injected varied between 80,000 (red) 300,000 (yellow), 400,000 (violet) and 500,000 (white and blue) to account for the different absorbance characteristics of the CM. On the day of the experiment, the previously portioned and dried CM were suspended in 3 ml saline (containing 0.02% Tween 80) for intracoronary injection and 6 ml saline (containing 0.02% Tween 80) for intraatrial injection and ultrasonicated for 1 min. Each microsphere injection was followed by a flush of saline solution. For each measurement in the four dogs, approximately $3 \times 10^6$ RM and $1.8 \times 10^6$ (red) to $7 \times 10^6$ (white, yellow, violet and blue) CM were injected. After occlusion of the LAD even more colored spheres ($20 \times 10^6$) were injected to improve the precision of RMBF measurements in the low flow situation. Stable steady state conditions of systemic hemodynamics, regional myocardial function and coronary blood flow before and during microsphere infusion and the withdrawal period were assured under each condition in all experiments. In the dog studies with left atrial injection, reference arterial blood samples were collected through the aortic catheter starting 10 s before injection of the microspheres and continuing for 100 s at a rate of 6.3 ml/min.

Five different myocardial blood flow conditions were produced for both the pigs and dogs. During steady state conditions, one pair of colored and randomly matched RM was simultaneously injected.

In the four pigs, the first RMBF measurement was performed under baseline conditions. LAD blood flow was then increased in three steps by intracoronary adenosine infusion (100–400 ug/min) at a constant coronary perfusion pressure, and measurements were again performed at stable steady states of elevated flow. Finally, coronary perfusion pressure was reduced to produce regional myocardial akinesia, and a last measurement was performed during steady state ischemia.

In the four dogs, after control measurements coronary blood flow was increased in three steps by intravenous infusion of dipyridamole (0.1–0.3 mg/kg) and epinephrine (0.5–3 ug/(kg.min)), and measurements were performed at the respective steady rates. A final measurement was begun after 3 min complete occlusion of the LAD during steady state regional myocardial dysfunction.

After completion of the study, animals were euthanized. The hearts were removed and carefully dissected free from epicardial fat. In the four dogs of protocol 1 and in the four pigs of protocol 2, the LAD-perfused myocardium was delineated by methylene-blue injection into the perfusion line prior to euthanization. The stained myocardium was cut into samples of 0.3 to 1.8 g (mean 1.1 g) and placed into teflon-sealed 16 ml screw-cap glass tubes (Schott, Mainz, FRG). The mean number of samples per animal was 54 in the four pigs of protocol 2 and 91 in the four dogs of protocol 3. The left ventricular samples were divided into transmural thirds. In the four dogs of protocol 3, both ventricles and atria were processed in the same way. After counting y-radioactivity in a 3-in. NaI (Til) well detector (Model BF5300, Berthold, Wildbad, FRG) for 1 min with a multichannel pulse-height analyzer, the samples were processed for CM quantification.

7 ml of a 4M KOH solution containing 2% Tween 80 were added to each sample for digestion of the tissue. The glass tubes were closed, placed in a water bath shaker for 4 hours at 72° C. and hand-mixed every hour. A high-grade steel vacuum filtration chamber was fitted to a polyester filter (pore size 8 micrometer, diameter 25 mm, Nuclepore, Tubingen, FRG). The digested tissue solution was mixed with a teflon-coated magnetic stirring bar and then placed on the filter with a burette, rinsing the filter with 2% Tween 80 solution, which was then filtered just as the tissue solution before.

The reference blood samples were processed in the same manner as the tissue samples. Each blood sample and the 2% Tween 80 washing fluid (7 ml twice) of the blood withdrawal syringe were divided into 3.5 ml portions for the counting of RM. For subsequent digestion, 1.1 ml 16M KOH and 0.5 ml 20% Tween 80 solution were added. Thus, the KOH- and Tween 80-concentrations were the same as in the tissue samples. The further preparation of the blood samples was not different from that of the tissue samples.

For use in the calculation of RMBF in the pigs (protocol 2), the radioactivity and dye content of the entire perfusion area were determined. Hence, in the four pigs RMBF, corrected for wet weight, was calculated using the equation: (X per sample/blood flow to sample)=(total tissue X/coronary inflow), where X is the number of counts per min for the RM or the specific absorbance for the CM (See Schulz et al, supra). The total tissue radioactivity content was determined by totalling all counts from the perfusion bed whereas the amount of dye injected was determined by totalling the absorbance of all samples. Coronary inflow was set by the extracorporeal coronary perfusion circuit. In the dogs (protocol 3) RMBF, corrected for wet weight of the tissue, was calculated using standard techniques (See Makowski et al, supra): (X per sample/blood flow to sample)=(X in arterial withdrawal/reference withdrawal rate).

4. Comparisons of the method of the present invention to other microsphere RMBF measurement techniques The time requirements of the method of the present invention are superior. For all RMBF techniques, cutting and weighing of tissue samples is necessary. Using the method of the present invention, the further processing of an individual tissue or blood sample requires approximately 8-10 min and an additional 3 min for the spectrophotometric measurement. For all samples together, an additional 4 hours are necessary for the digestion procedure. Using the technique proposed by Hale et al, supra, processing of an individual sample requires 45 min. However, the time for microscopic counting of an aliquot of microspheres in a hemacytometer was not mentioned. Using the technique proposed by Morita et al, supra, tissue samples have to be further cut to achieve a homogeneous distribution within the irradiated volume of the vial, and blood samples have to be further processed and suspended in gelatin for a homogeneous distribution of microspheres in the vial. The measurement as such requires an additional 10 min per sample.

The present invention is of superior economy. The costs for the measurement of RMBF under 5 different flow conditions in a 30 kg dog, including preparation and dyeing of our CM as well as tissue and blood processing of 100 samples, amount to approximately $150. No special and expensive disposal of carcasses is necessary. Shelf life of CM in accordance with the present invention is not limited as is that of RM which are subject to individually different half-life characteristics. Such differential decay times makes keeping inventories complex and causes additional costs. Measurement of only 4 flow situations and processing of only 10 tissue samples and 4 blood samples cost $350 using the method proposed by Hale et al, supra. Using RM from DuPont NEN Products, five flow measurements also cost approximately $350. Information about the costs of microspheres using the technique of Morita et al, supra, is not available.

The equipments used in the method of the present invention are standard. Laboratory equipment for microsphere dyeing and sample processing (centrifuge, ultrasonicator, vortex mixer, magnetic stirrer, shaking water bath, glass ware) cost approximately $15,000. However most of this equipment will be already available to most laboratories. The cost of the counting unit is approximately $15,000 for the spectrophotometer, as compared to approximately $40,000 for a sodium-iodide gamma-counter including an autosampler. For the technique proposed by Hale et al, supra, a light microscope and a hemacytometer are required, again besides standard laboratory equipment (centrifuge, ultrasonicator, vortex mixer, water bath, glass ware). The equipment for X-ray fluorescence excitation and detection according to the technique of Morita et al, supra, is estimated to cost approximately $120,000.

5. Analysis of Data Obtained With the Method of the Present Invention

The regression analyses were based on a least squares fitting method using the commercial software program on an IBM compatible personal computer type AT. To test the hypothesis that measurement of RMBF would be identical using RM and CM, slope and intercept were compared to the line of identity (intercept=0, slope=1) by two-tailed F-tests.

6. Effectiveness Studies and Results 6.1 In Vitro Studies

Figure 5:
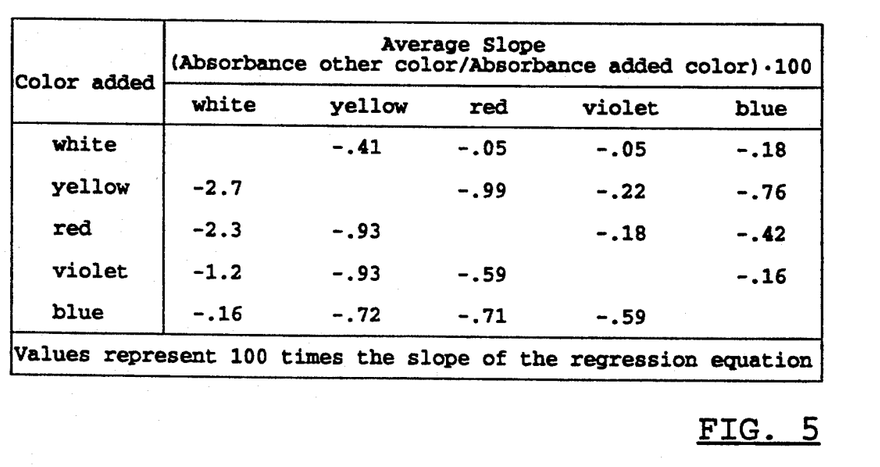
FIG. 5 shows a Table 1 containing data on interactions for a five-color set of colored microspheres (CM) in accordance with the present invention.

The interaction of single colors within a composite spectrum was negligible, as evidenced by minimal changes in the absorbance of a given four color-set by adding increasing concentrations of a fifth color, are shown in Table 1 of FIG. 5.

Figure 6:
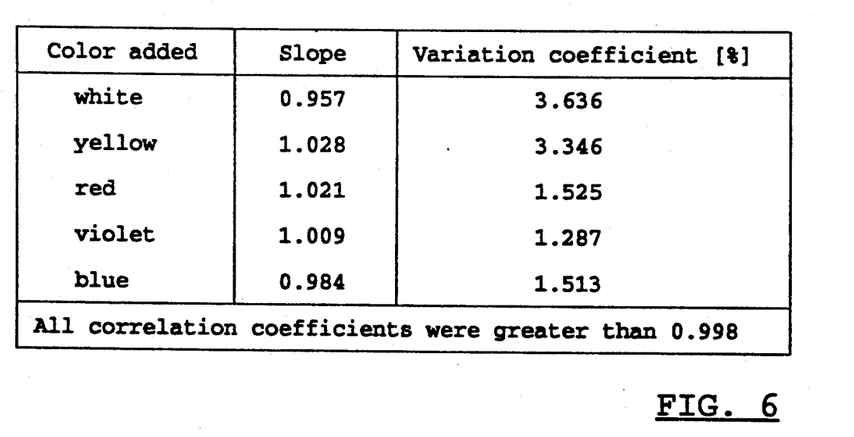
FIG. 6 shows a Table 2 containing data on recoveries for a five-color set of colored microspheres (CM) in accordance with the present invention.

The recovery of dye by matrix inversion resolution of composite spectra was almost complete, since slopes of regression lines between the real and the calculated absorbance values were within 5% of the line of identity. This is shown in Table 2 of FIG. 6.

The chi squared value as an indicator of the goodness of separation of colors by spectrophotometry and matrix inversion was between 50 and 200, and the variation coefficient determined for each calculated absorbance value by use of the respective chi squared was less than 1% for each color.

6.2 In Vivo Studies

Figure 7:
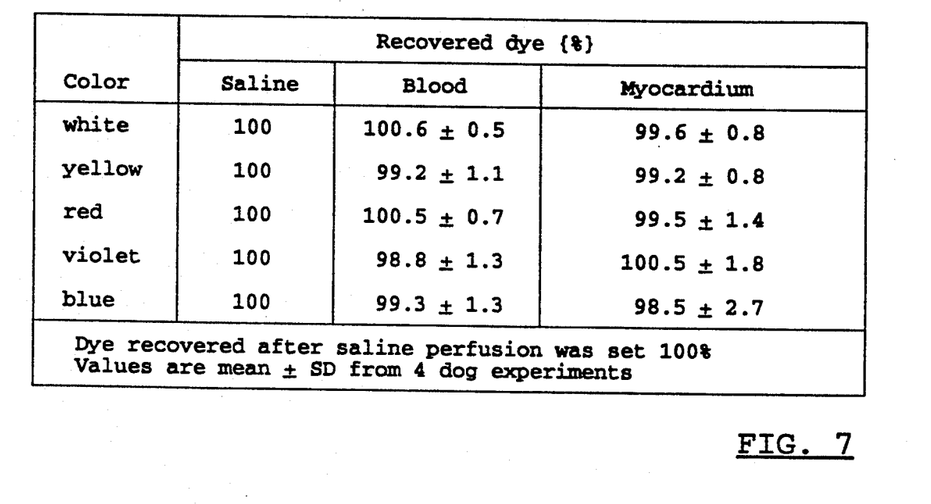
FIG. 7 shows a Table 3 containing data on the stability of the dye-attachment in vivo to a five-color set of colored microspheres (CM) in accordance with the present invention.

A significant leaching of dye from microspheres either injected into blood ex vivo or trapped in myocardium in vivo during an 8 hour period did not occur for any color, as compared to the immediately processed microspheres exposed to saline only. This is shown in Table 3 of FIG. 7.

Figure 3A:
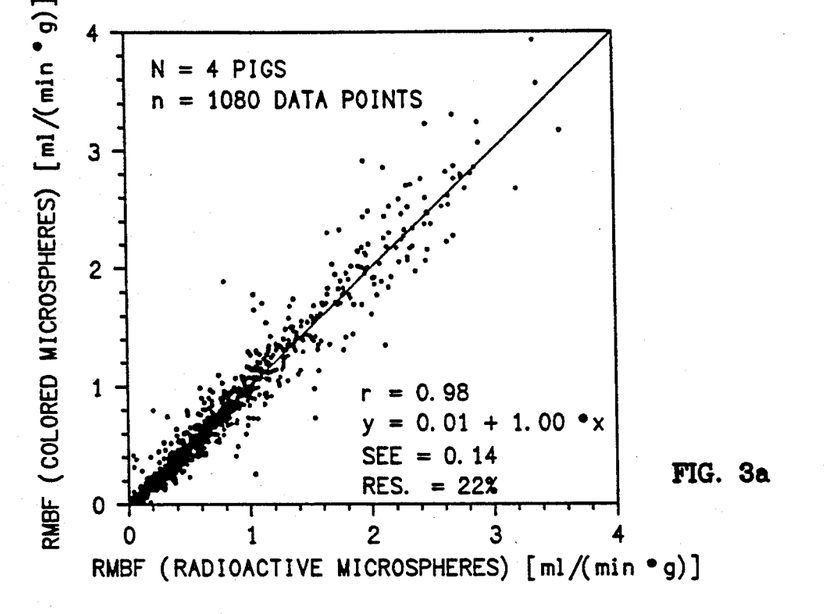
FIG. 3a is a graphical regression plot of all regional myocardial blood flow (RMBF) values (n=1080) measured by radioactive microspheres (RM), and alternatively by colored microspheres (CM) in accordance with the present invention, during systematic flow variations in 4 pigs using intracoronary microsphere injection. Each point represents one tissue sample. SEE=-standard error of the estimate; RES=mean percentage of the residuals.
Figure 3B:
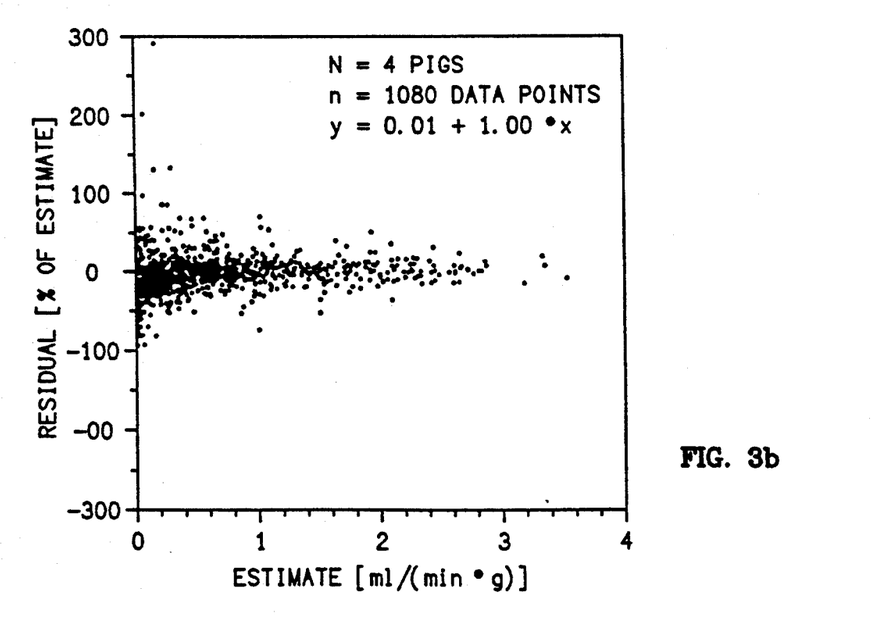

In the pigs, in a total of 1080 samples RMBF measured by intracoronary injection of RM and CM was almost identical. The linear regression was not different from identity (FIG. 3). Subdividing the regression into low to normal ($\leq 1.1$ ml/(min g)) and normal to high flows ($\geq 1.1$ ml/(min g)) revealed no differences in either slopes or intercepts.

Figure 4A:
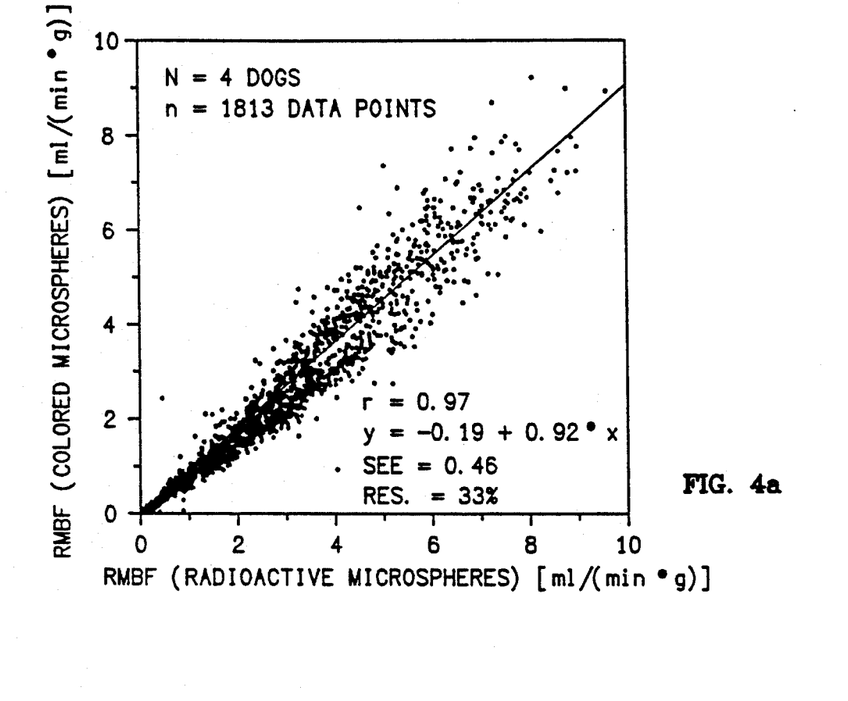
FIG. 4a is a graphical regression plot of all regional myocardial blood flow (RMBF) values (n-1813) measured by radioactive microspheres (RM), and alternatively by colored microspheres (CM) in accordance with the present invention, during systematic flow variations in four (4) dogs using left atrial microsphere injection. Each point represents one tissue sample. SEE=standard error of the estimate; RES=mean percentage of the residuals.
Figure 4B:
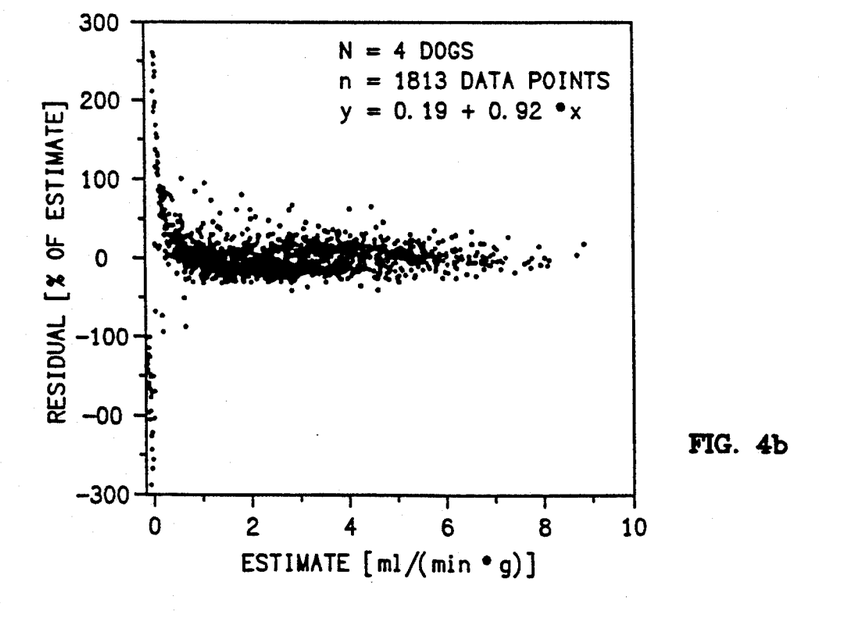
Figure 8:
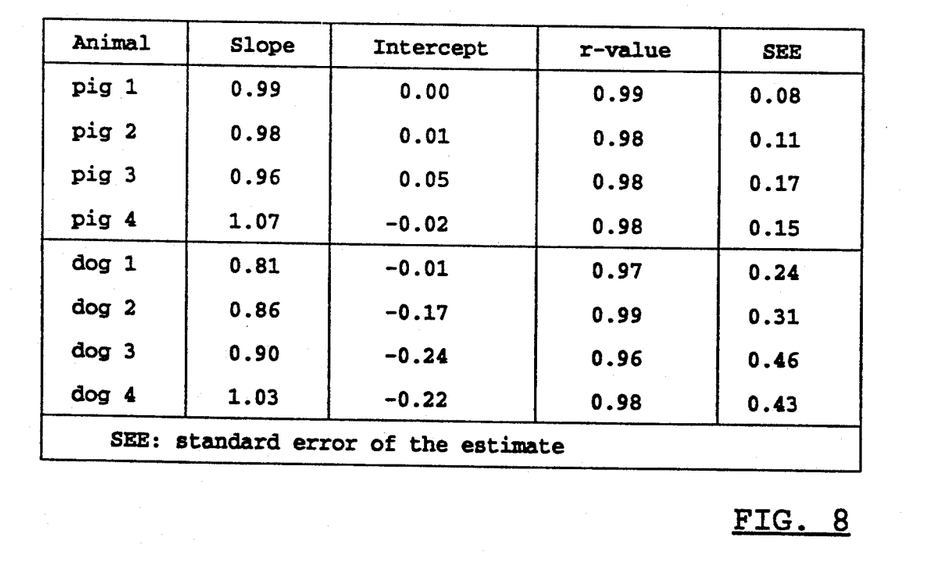
FIG. 8 shows a Table 4 containing experimental regression data for individual animals (dogs) for which blood flow was analyzed with colored microspheres (CM), and methods, of the present invention.

In the dogs, in a total of 1813 samples RMBF measured by itraatrial injection of CM and RM correlated closely. The correlations for individual animals are shown in Table 4, FIG. 8. RMBF determined with CM was systematically somewhat lower, as indicated by the slope of the regression line shown in FIG. 4. Subdividing the regression into low to normal ($\leq 1.1$ ml/(min g)) and normal to high flows ($\geq 1.1$ ml/(min g)) revealed a lower slope for lower flows (0.78) and a higher slope for higher flows (0.94).

The relationship between RMBF determined by CM and RM was: CM=0.01+1.00 RM ($r=0.98$, $n=1080$ data points) in the pigs, and CM=$-0.19+0.92$ RM ($r=0.97$, $n=1813$ data points) in the dogs. Measurement of RMBF with CM yields very similar values as with RM. Their use is less expensive and avoids all disadvantages related to radioactivity, thus offering an alternative method for up to 5 RMBF measurements in a single experiment.

7. Discussion of the Studies and Results

The explanation herein demonstrates that RMBF can be accurately measured using a cost-effective, non-radioactive technique which currently allows up to 5 measurements in a single experimental preparation.

In the in vitro studies, the CM technique of the present invention proved to be equally good as the established RM technique. The size distribution of CM in accordance with the present invention is highly uniform whereas the CM used by Hale et al, supra, varied in diameter from 3.3 to 29.2 um. The density of CM in accordance with the present invention is 1.09 g/ml, thus closely approximating the density of erythrocytes. The density of the CM used by Hale et al, supra, is somewhat lower (1.05 g/ml) whereas RM have a density of 1.3 g/ml, and the density of the non-radioactive microspheres proposed by Morita et al, supra, is even above 2 g/ml. A significant leaching of the label from the microspheres did not occur with the CM of the present invention. The separation characteristics employing spectrophotometry and matrix inversion resolution of composite spectra revealed almost complete recovery of each dye and only minimal interaction between different dyes of a composite spectrum (Tables 1 and 2, FIGS. 5 and 6). Also, the variation coefficients calculated from chi squared values using an overdetermined set of linear equations as previously applied by Baer et al, supra, to RM were less than 1%.

In the in-vivo studies, no significant leaching of the dyes from the microspheres occurred during an 8 hour period in blood or in myocardium. The small deviation from the saline reference (Table 3, FIG. 7) is well within the accuracy of pipetting multiple identical aliquots or the shunting of microspheres from myocardium. See Utley J., Carlson E. L., Hoffman J. I. E., Martinez H. M., Buckberg G. D.: Total and regional myocardial blood flow measurements with 25 u, 15 u, 9 u, and filtered 1–10 u diameter microspheres and antipyrine in dogs and sheep. Circ Res 1974;34:391–404. See also Fan F. C., Schuessler G. B., Chen R. Y. Z., Chien S.: Determinations of blood flow and shunting of 9 - and 15 -um spheres in regional beds. Am J Physiol 1979;237:H25–H33.

During in-vivo validation of CM versus RM, higher numbers of CM than of RM were used for the measurement of RMBF. However, left atrial injection of $13 \times 10^6$ microspheres (See von Ritter C., Hinder R. A., Womack W., Bauerfeind P., Fimmel C. J., Kvietys P. R., Granger D. N., Blum A. L.: Microsphere estimates of blood flow: methodological considerations. Am J Physiol 1988;254:G275–G27) or serial injections of up to $48 \times 10^6$ microspheres (see Baer, supra) have been reported to be without significant effects on systemic hemodynamics. Thus, the injection of this many CM did obviously not result in a critical embolization of the coronary vasculature in our experiments. That would have been indicated by a deterioration of regional myocardial function, which correlates closely with myocardial perfusion under ischemic conditions. See Gallagher K. P., Kumada T., Koziol J. A., McKown M. D., Kemper W. S., Ross J. Jr.: Significance of regional wall thickening abnormalities relative to transmural myocardial perfusion in anesthetized dogs. Circulation 1980;62:1266–1274.

After intracoronary administration, there was no difference in RMBF measured by CM or RM. However, after intraatrial injection, RMBF calculated from RM was slightly higher than that determined with CM. Whether this difference between RMBF measurements using CM and RM reflects an additional statistical error by the additional analysis of reference blood samples, or represents a systematical error introduced by the reference blood withdrawal as such, cannot be distinguished. Fewer RM than CM being sampled in the reference blood withdrawal relative to the myocardium would result in a higher RMBF calculated from RM than from CM. However, a preferential streaming of RM with the direction of higher flow, e.g. aorta versus the withdrawal syringe, has only been documented for microspheres of larger diameter (See, for example, Phibbs R. H., Wyler F., Neutze J.: Rheology of microspheres injected into circulation of rabbits. Nature 1967;216:1339–1340; and also Phibbs R. H., Dong L.: Nonuniform distribution of microspheres in blood flowing through a medium-size artery. Can J Physiol Pharmacol 1970;48:415–421) but not for microspheres of equal diameter and different density (see, for example, Reed J. H. Jr., Wood E. A.: Effect of body position on vertical distribution of pulmonary blood flow. J Appl Physiol 1970;28:303–311). In any event, the density of CM in accordance with the present invention is closer to that of erythrocytes and the difference between RMBF values using CM and RM is small.

In conclusion, measurement of RMBF with the technique of the present invention using CM yields very similar values as with RM. The technique of the present invention avoids all problems related to radioactivity and is cost-effective. To avoid radioactivity, more time for dyeing of microspheres and for tissue and blood sample processing is required, i.e., about 8 hours for preparing a batch of $100 \times 10^6$ CM and about 20 hours for processing of 100 samples. Potentially, this time can be reduced by future use of an autosampler in conjunction with the spectrophotometer. An extension for use of more colors is also conceivable. This technique enables laboratories, which have no access to RM, to measure RMBF and others to perform more sequential measurements.

7. Recapitulation of Selected Methodologies in Accordance with the Present Invention, and Possible Variants The present invention has thusly been seen to be embodied in a process for measuring a flow of fluid into a volume serving as a reservoir of the fluid. The process begins with the step of labeling microspheres by dyeing the microspheres a dye that has a quantitatively known photometric spectrum. The labeled microspheres are introduced into a stream of fluid flowing into the volume that serves as a reservoir for the fluid. The concentration of dye that is within the stream of fluid at the time of introduction, this concentration being in amount dye per unit time per unit portion of fluid, is then quantitatively determined. This determination gives a quantitative DENOMINATOR. Next, a sample including fluid from the volume, which sample had been supplied with fluid prior to its recovery, is recovered. A unit portion of the recovered sample is quantified, giving a quantified SAMPLE PORTION. The dye is extracted from all of such undetermined number of labeled microspheres as are within the SAMPLE PORTION. The photometric spectrum of the extracted dye is measured in order to determine the quantitative amount of dye that contributed thereto, and that was present within the SAMPLE PORTION. This measuring gives a quantitative number, an AMOUNT DYE. The AMOUNT DYE divided by the SAMPLE PORTION is calculated so as to give a quantitative number ultimately to be used as a NUMERATOR. Finally, the quantitative fluid flow rate to the sample per unit portion of the sample is calculated as the NUMERATOR divided by the DENOMINATOR.

The quantitative determination of the amount of dye that is within the stream of fluid can actually, and preferably, transpire by a procedure that is completely similar to, and consistent with, the later determination of the AMOUNT DYE that is within the recovered sample! Namely, an amount of the fluid is recovered at a predetermined rate. An interval during which this recovering transpires is timed, giving a TIME INTERVAL. From these two steps a quantitative AMOUNT FLUID recovered is calculated by multiplying the predetermined rate of recovering times the TIME INTERVAL. Continuing, a unit portion of the recovered fluid is quantified, this quantifying giving a quantitative FLUID PORTION. The dye is then extracted from all of such undetermined number of labeled microspheres as are within the FLUID PORTION. The photometric spectrum of the extracted dye is then measured in order to first determine the amount of the dye that contributed thereto, and that was present within the FLUID PORTION. This measuring gives a quantitative number, an AMOUNT DYE. Finally, the quantitative DENOMINATOR is calculated by dividing the AMOUNT DYE first by the TIME INTERVAL, and then, further, by the FLUID PORTION.

Alterations and adaptations of this basic method—distinguished for dealing with the amount of dye used in the fluid flow experiment as opposed to the numbers of microspheres (or whatever) upon or within which such dye is borne—are obviously possible. Many different dyes, potentially individually associated with different microspheres, can be place within the stream of flowing fluid in parallel, or seriatim. The amount of dye that accumulates in the volume is obviously but a double integration over time, and over the volume, of the calculated flow rate of the fluid into the volume per unit time per unit volume. Especially in use of the method of the present invention in blood flow analysis, substantially all the labeled colored microspheres that ever reach a particular sample of tissue will typically reach this sample within a few seconds or minutes, and will remain there forever after until the tissue is harvested, potentially after a delay of hours, days, weeks, months, or even years. Therefore, no excessive distinction should be made between determinations of fluid flow rates, or of fluid flow amounts, with the methods of the present invention—it being understood by a practitioner of the fluid flow arts that fluid flow rates, even those which are complex functions of time and/or of spatial volume, may be integrated to give fluid flow amounts.

Still further, the present invention has been seen to be embodied in fluid flow determination methods that are differentiated from full scale fluid flow analysis, and particularly from the sophisticated performance of blood flow analysis. One method in accordance with the present invention simply measures, for whatever reason or analysis, the amount of dye that is within a multiplicity of microspheres where each microsphere has an amount of a dye that has a known photometric spectrum. The microspheres may be lodged within a volume. If so, the method commences by extracting the microspheres from the volume. Next, the dye content of the extracted microspheres is drawn off into a predetermined volume of solvent, forming thereby a predetermined volume of dye-solution. The photometric spectrum of the dye-solution is then measured as an indication of the amount of dye therein, and thus the amount of dye that was within the extracted microspheres, and thus the amount of dye that was within the volume.

In accordance with these and other adaptations and alterations of the present invention, the invention should be interpreted broadly, in accordance with the language of the following claims only, and not solely in accordance with those particular embodiments within which the invention has been taught.

What is claimed is:

1. A process for measuring a flow of a fluid into a volume serving as a reservoir of the fluid, the process comprising the steps of:

labeling microspheres by dyeing the microspheres with a dye that has a quantitatively known photometric spectrum;

introducing a predetermined amount of the labeled microspheres into a stream of the fluid that flows into the volume that serves as the reservoir for the fluid;

determining a concentration of the dye that is within the stream of fluid at the time of, and as a consequence of, said step of introducing the labeled microspheres, the concentration being in amount dye per unit portion of fluid per unit time, this step of determining giving a quantitative DENOMINATOR;

recovering a sample including the fluid and the labeled microspheres from the volume, which sample had been supplied with the fluid into which the labeled microspheres had been introduced prior to its recovery;

quantifying a unit portion of the recovered sample, said step of quantifying giving a quantified SAMPLE PORTION;

extracting the dye from all of the labeled microspheres that are within the SAMPLE PORTION;

measuring the photometric spectrum of the extracted dye in order to determine the quantitative amount of dye that contributed thereto, and that was present within the SAMPLE PORTION, said step of measuring giving a quantitative AMOUNT DYE;

calculating the AMOUNT DYE divided by the SAMPLE PORTION, said step of calculating giving a quantitative NUMERATOR; and calculating a quantitative fluid flow to the sample per unit portion of the sample as the NUMERATOR divided by the DENOMINATOR.

2. The process according to claim 1 wherein the step of labeling comprises the sub-step of:

infusing a predetermined number of microspheres with a predetermined amount of dye in solution.

3. The process according to claim 1 wherein the step of determining comprises the sub-steps of:

recovering an amount of the fluid at a predetermined rate;

timing an interval during which the sub-step of recovering transpires, said sub-step of timing giving a TIME INTERVAL;

quantifying a unit portion of the recovered fluid, said sub-step of quantifying giving a quantitative FLUID PORTION;

extracting the dye from all of the labeled microspheres that are within the FLUID PORTION;

measuring the photometric spectrum of the extracted dye in order to first determine the amount of the dye that contributed thereto, and that was present within the FLUID PORTION, said sub-step of measuring giving a quantitative AMOUNT DYE; and calculating the DENOMINATOR by first dividing the AMOUNT DYE by the FLUID PORTION, and then, further, second dividing by the TIME INTERVAL.

4. The process for measuring a flow of fluid according to claim 3
wherein the step of determining of the DENOMINATOR is in units of amount dye in absorbance or emission units, per milliliter per minute and
the sub-step of recovering at the predetermined rate is in units of milliliters per minute,
the sub-step of timing of the TIME INTERVAL is in units of minutes,
the sub-step of quantifying of the FLUID PORTION is in units of milliliters,
the sub-step of measuring of the AMOUNT DYE is in absorbance or emission units respectively as the measuring is of the photometric spectrum of absorption or of fluorescence, and
the sub-step of calculating of the DENOMINATOR is thus in units of absorbance or emission units, per milliliter per minute;
wherein the step of quantifying of the SAMPLE PORTION is in gram units;
wherein the step of measuring of the AMOUNT DYE is in absorbance or emission units respectively as the measuring is of the photometric spectrum of absorption or of fluorescence;
wherein the step of calculating the NUMERATOR is thus in units of absorbance or of emission, per gram; and
wherein the step of calculating the quantitative fluid flow to the sample per unit portion of the sample is thus in units of milliliters per minute per gram.

5. The process for measuring a flow of fluid according to claim 1 adapted for measuring blood flow in an animal
wherein the step of introducing is a step of introducing the labeled microspheres into the blood stream of an animal;
wherein the step of determining is a step of determining the concentration of the dye that is within the blood stream of the animal at the time of the introduction, the concentration being in amount of dye per unit portion of blood per unit time;
wherein the sample is a sample of the animal's tissue which tissue sample had been supplied with the blood prior to recovery;
wherein the step of quantifying is of a unit portion of the recovered tissue sample;
wherein the step of extracting of the dye is from all of the labeled microspheres that are within the unit portion of the recovered tissue sample;
wherein the step of measuring of the photometric spectrum of the extracted dye is in order to quantitatively determine the amount of the dye that contributed thereto, and that was present within the unit portion of the recovered tissue sample;
wherein the step of calculating the NUMERATOR is of amount of dye that was present within the recovered tissue sample divided by the unit portion of the recovered tissue sample; and
wherein the step of calculating the quantitative fluid is of a quantitative blood flow rate to the tissue per unit portion of the tissue.

6. The process according to claim 5 wherein the step of labeling comprises the sub-step of:
infusing a predetermined number of microspheres with a predetermined amount of the dye in solution.

7. The process according to claim 5 wherein the step of determining comprises the sub-steps of:
recovering a sample of the animal's blood at a predetermined rate;
timing an interval during which the sub-step of recovering transpires, said sub-step of timing giving a TIME INTERVAL;
quantifying a unit portion of the recovered blood, said sub-step of quantifying giving a quantitative BLOOD PORTION;
extracting the dye from all of the labeled microspheres that are within the BLOOD PORTION;
measuring the photometric spectrum of the extracted dye in order to first determine the amount of the dye that contributed thereto, and that was present within the BLOOD PORTION, said sub-step of measuring giving a quantitative AMOUNT DYE; and
calculating the DENOMINATOR by first dividing the AMOUNT DYE by the BLOOD PORTION, and then, further, second dividing by the TIME INTERVAL.

8. The process according to claim 1 wherein the step of labeling comprises the sub-step of:
non-radioactively quantitatively labeling the microspheres with a colored dye that has a quantitatively know photometric spectrum of absorption;
and wherein the step of quantitatively measuring comprises the sub-step of:
quantitatively measuring the photometric absorption spectrum of the extracted dye.

9. The process according to claim 1 wherein the step of labeling comprises the sub-step of:
non-radioactively quantitatively labeling the microspheres with a fluorescent dye that has a quantitatively known photometric spectrum of emission when stimulated by appropriate radiation; and
wherein the step of quantitatively measuring comprises the sub-steps of:
stimulating the extracted dye with radiation appropriate so as to induce its fluorescence; and
quantitatively measuring the photometric emission spectrum of the radiation-stimulated extracted dye.

10. A process for measuring a flow of blood into a tissue of an animal, the process comprising the steps of:
labeling microspheres by dyeing the microspheres with a dye that has a quantitatively known photometric spectrum;
introducing a predetermined amount of the labeled microspheres into the blood in a blood stream of the animal;
determining a concentration of the dye that is within a unit portion of the blood stream per unit time at a time after introduction, said step of determining giving a quantitative DENOMINATOR;
recovering a sample to the tissue including the blood into which the labeled microspheres had been introduced from the animal;
quantifying a unit portion of the recovered tissue sample;
extracting the dye from all of such undetermined number of labeled microspheres as are within the unit portion of the tissue sample;
measuring the photometric spectrum of the extracted dye in order to determine the quantitative amount of dye that contributed thereto, and that was present within the unit portion of the tissue sample, said step of measuring giving a quantitative AMOUNT DYE;

first-calculating the AMOUNT DYE divided by the unit portion of the tissue sample, said step of first-calculating giving a quantitative NUMERATOR; and second-calculating quantitative blood flow to the tissue sample per unit portion of the tissue sample as the NUMERATOR divided by the DENOMINATOR.

* * * * *